(12) United States Patent
Kopkalli et al.

(10) Patent No.: US 8,618,340 B2
(45) Date of Patent: *Dec. 31, 2013

(54) INTEGRATED PROCESS FOR FLUORO-OLEFIN PRODUCTION

(75) Inventors: Haluk Kopkalli, Staten Island, NY (US); Yuon Chiu, Denville, NJ (US); Stephen A. Cottrell, Baton Rouge, LA (US); Hsueh Sung Tung, Getzville, NY (US); Kevin Uhrich, Alden, NY (US)

(73) Assignee: Honeywell International Inc., Morriston, NJ (US)

(*) Notice: Subject to any disclaimer, the term of this patent is extended or adjusted under 35 U.S.C. 154(b) by 279 days.

This patent is subject to a terminal disclaimer.

(21) Appl. No.: 12/611,288

(22) Filed: Nov. 3, 2009

(65) Prior Publication Data

US 2011/0105807 A1 May 5, 2011

(51) Int. Cl.
*C07C 23/18* (2006.01)

(52) U.S. Cl.
USPC ........... 570/188; 570/135; 570/155; 570/157; 570/164; 570/179

(58) Field of Classification Search
None
See application file for complete search history.

(56) References Cited

U.S. PATENT DOCUMENTS

| 7,345,209 | B2 | 3/2008 | Mukhopadhyay et al. | |
|---|---|---|---|---|
| 2007/0197842 | A1* | 8/2007 | Mukhopadhyay et al. | ... 570/155 |
| 2009/0030244 | A1 | 1/2009 | Merkel et al. | |
| 2009/0030247 | A1 | 1/2009 | Johnson et al. | |
| 2009/0043136 | A1 | 2/2009 | Wang et al. | |
| 2009/0099396 | A1 | 4/2009 | Mukhopadhyay et al. | |
| 2009/0240090 | A1 | 9/2009 | Merkel et al. | |

FOREIGN PATENT DOCUMENTS

| EP | 2103587 | 9/2009 |
|---|---|---|
| WO | 2007079431 | 7/2007 |
| WO | 2008054778 A2 | 5/2008 |
| WO | 2008054782 A1 | 5/2008 |
| WO | 2008060614 A2 | 5/2008 |
| WO | 2009035130 A2 | 3/2009 |

OTHER PUBLICATIONS

Kim, et al., "A Study to Determine the Existence of an Azeotropic R-22 "Drop-In" Substitute," prepared by U.S. Department of Commerce for Electric Power Research Institute, Mar. 1996, pp. 1-45, U.S.

Morrison, et al., "Azeotropy in Refrigerant Mixtures," International Journal of Refrigeration, 1993, pp. 129-138, vol. 16, No. 2. U.S.

* cited by examiner

*Primary Examiner* — Sudhakar Katakam
(74) *Attorney, Agent, or Firm* — Bruce O. Bradford

(57) ABSTRACT

Disclosed is a process for the manufacture of HFO-1234yf from TCP in three integrated steps that include hydrofluorination of TCP (tetrachloropropene) to HCFC-1233xf in the vapor phase followed by hydrofluorination of HCFC-1233xf to HCFC-244bb in the liquid phase which is then followed by dehydrochlorination in liquid or vapor phase to produce HFO-1234yf. The vapor phase hydrofluorination is carried out at a higher pressure than the liquid phase hydrofluorination, thereby eliminating the need for compression and/or intermediate recovery. Also, any HCl generated from this reaction is fed to the liquid phase hydrofluorination section to promote agitation and mixing. This results in a more economical process from an initial capital and operating cost versus conducting the 3-steps sequentially.

28 Claims, 1 Drawing Sheet

Block Flow Diagram for Production of HFO-1234yf from TCP
Scheme 1
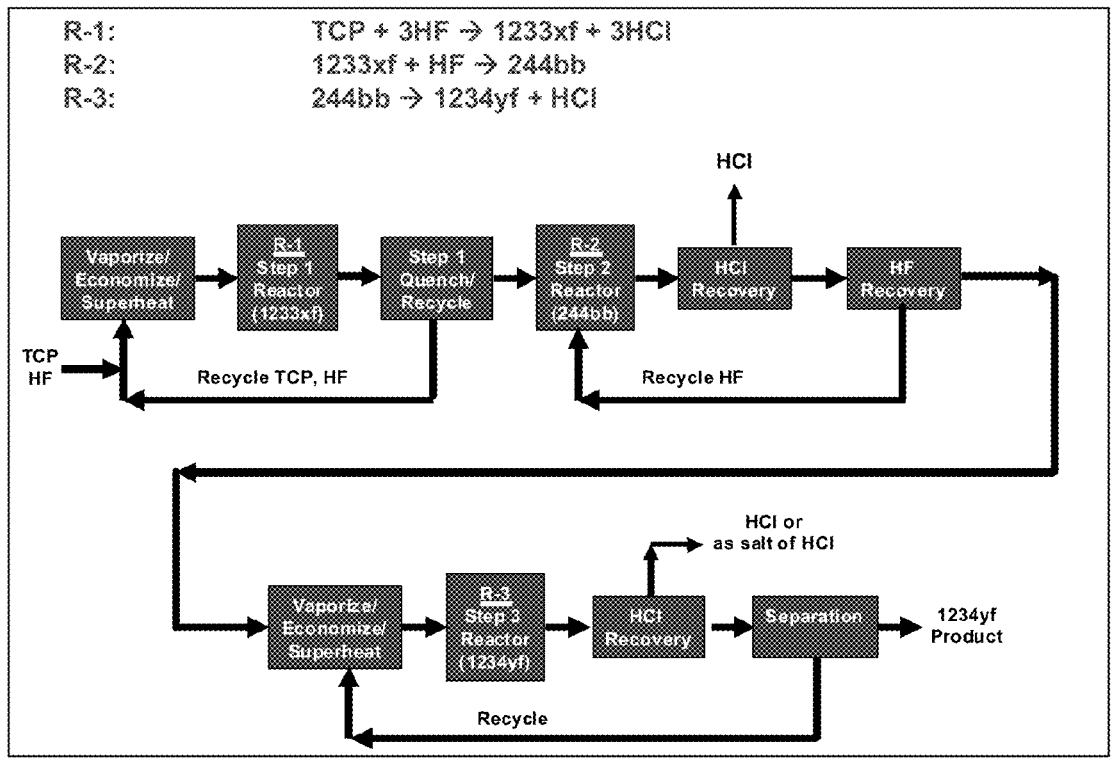
Scheme 2
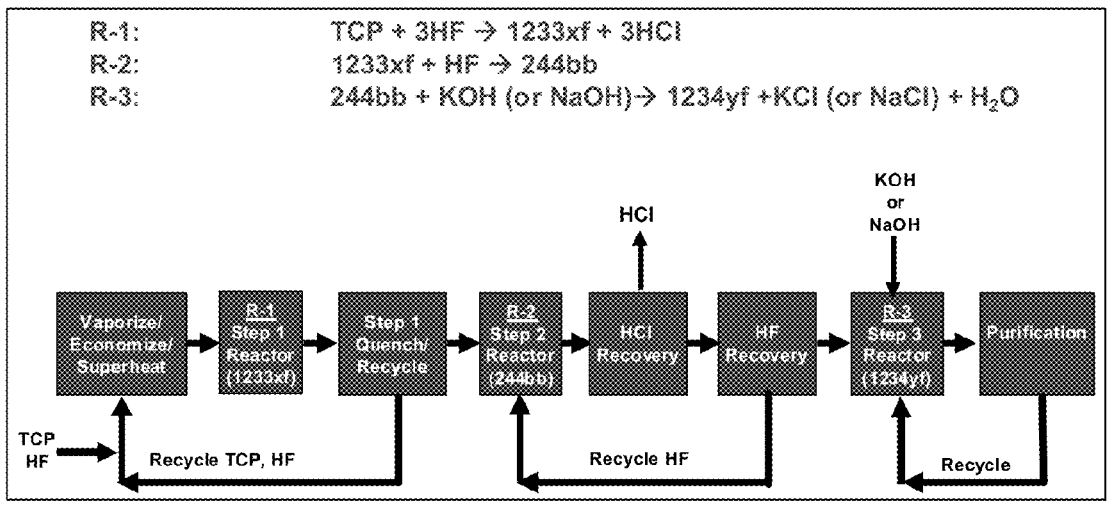

US 8,618,340 B2

INTEGRATED PROCESS FOR FLUORO-OLEFIN PRODUCTION

FIELD OF THE INVENTION

Fluorocarbons, particularly fluorinated olefins, as a class, have many and varied uses, including as chemical intermediates and monomers. In particular, the hydrogenated products are useful as refrigerants, monomers or intermediates for preparing refrigerants, particularly those identified as having low global warming potential.

BACKGROUND OF THE INVENTION

This invention relates to the production of 2,3,3,3-tetrafluoro-2-propene, also known as HFO-1234yf, and known also by the chemical formula; $CF_3$—$CF$=$CH_2$. This chemical compound has zero ozone depletion potential and very low global-warming potential such that it may be useful and desirable as a replacement for existing materials used in refrigeration, foam blowing and other applications where fluorocarbons such as 1,1,1,2-tetrafluoroethane, also known as HFC-134a, and known also by the chemical formula; $CH_2F$—$CF_3$, are currently utilized.

It is known in the art to produce HFO-1234yf from 1,1,2,3-tetrachloropropene (TCP or $CCl_2$=$CCl$—$CH_2Cl$) using a non-integrated three step route; see for example US Publication No. 2007/0197842, the disclosure of which is hereby incorporated herein by reference.:

TCP+3HF→HCFC-1233xf+3HCl (where HCFC-1233xf is $CH_2$=$CCl$—$CF_3$)

HCFC-1233xf→HCFC-244bb (where HCFC-244bb is $CF_3$—$CFCl$—$CH_3$)

HCFC-244bb→HFO-1234yf+HCl

Other processes are likewise taught in the art. See, for example, the following references which are hereby incorporated herein by reference:

U.S. Pat. No. 7,345,209 discloses a process for the synthesis of 1,3,3,3-tetrafluoro-2-propene (HFO-1234ze).

U.S. Publication No. 2009/0099396 discloses a process for the synthesis of fluorinated olefins including 2,2,3,3-tetrafluoro-2-propene (HFO-1234yf).

U.S. Publication No. 2009/0043136 discloses a process for the preparation of fluorinated olefins via catalytic dehydrohalogenation of halogenated hydrocarbons.

U.S. Publication No. 2009/0030247 discloses a method for producing fluorinated organic compounds including 2,3,3,3-tetrafluoro-2-propene (HFO-1234yf).

U.S. Publication No. 2009/0030244 discloses a method for producing 2-chloro-3,3,3-trifluoropropene (HCFC-1233xf).

PCT Publication No. WO2009035130 discloses a process for the production of fluorinated olefins.

PCT Publication No. WO2009035130 discloses a process for the production of 2,3,3,3-tetrafluoro-2-propene (HFO-1234yf).

PCT Publication No. WO2008060614 discloses a process for the production of 2,3,3,3-tetrafluoro-2-propene (HFO-1234yf).

PCT Publication No. WO2008054782 discloses a process for the production of fluoropropanes and halopropanes.

PCT Publication No. WO2008054778 discloses a process for the production of 2,3,3,3-tetrafluoropropene, a process for producing 1-chloro-2,3,3,3-pentafluoropropane and azeotropic compositions of 1-chloro-2,3,3,3-tetrafluoropropene with HF.

SUMMARY OF THE INVENTION

This invention provides an integrated process which will decrease the amount of processing equipment required for the process, hence reducing the capital investment and operating cost, when comparing to a conventional design approach which required separate equipment to produce and isolate each individual process intermediate before subjecting it to further reaction. Hence, this invention provides a much more economical process both from capital and operating standpoints.

A process for the manufacture of HFO-1234yf from TCP in three integrated steps that include:

(R-1) hydrofluorination of TCP (tetrachloropropene) to HCFC-1233xf in the vapor phase;

(R-2) hydrofluorination of HCFC-1233xf to HCFC-244bb in the liquid phase or vapor phase or liquid phase followed by vapor phase; and (R-3) dehydrochlorination in liquid or vapor phase to produce HFO-1234yf.

Preferably, the vapor phase hydrofluorination is carried out at a higher pressure than the liquid phase hydrofluorination. Advantageously, any HCl generated from the first hydrofluorination reaction is fed to the second hydrofluorination section.

Preferably, the hydrofluorination of TCP to HCFC-1233xf occurs in the vapor phase in the presence of a fluorination catalyst in a reactor selected from the group consisting of; a single reactor, a multistage reactor, or a series of reactors; using a combination of recycle streams, fresh HF and fresh TCP. The fluorination catalyst is at least one of the following selected from the group consisting of $Cr_2O_3$, Sb/C, $FeCl_3$, $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$.

Preferably, the hydrofluorination of HCFC-1233xf to HCFC-244bb in the liquid phase (or liquid phase followed by vapor phase) further includes treatment of any reactor effluent containing HCFC-1233xf, HCl, excess HF and any unreacted TCP plus intermediates, by feeding this stream into a Quench/Recycle Column for separation of unreacted TCP and excess HF for recycle use in step R-1 of the process.

Preferably, the HCFC-1233xf, HCl and HF is fed to a liquid phase reactor containing catalyst selected from $SbCl_3$, $SbCl_5$, $SbF_5$, $TiCl_4$, $SnCl_4$ and combinations thereof for hydrofluorination of HCFC-1233xf to 1,1,1,2-tetrafluoro-2-chloropropane (HCFC-244bb). Preferably, a mixture of HCFC-244bb, HCl, unreacted HCFC-1233xf and HF exit the liquid reactor system via a catalyst stripper which is used such that most of the unreacted HF and catalyst is refluxed back to the reactor.

Preferably, the effluent from the catalyst stripper may be passed through a bed containing $SbCl_5$/Carbon catalyst for further conversion of HCFC-1233xf to HCFC-244bb. Advantageously, the effluent from the catalyst stripper or the effluent from $SbCl_5$/C bed is fed to an HCl column to separate essentially pure HCl in the overhead from the mixture of HCFC-244bb, HCFC-1233xf, HF and HCl.

Preferably, the HCl generated during the process is either recovered as is or passed through silica gel for residual HF removal and absorbed into water to produce hydrochloric acid.

Advantageously, the mixture of HCFC-244bb, HCFC-1233xf, HF is fed to an HF Recovery section for recovery and recycle of a stream rich in HF and another stream that is rich in HCFC-244bb and HCFC-1233xf. One such method is cooling the mixture of HCFC-244bb, HCFC-1233xf, HF and subjecting to phase separation to separate an organic layer and an HF layer. Another method is the treatment of the mixture of HCFC-244bb, HCFC-1233xf, HF with a solution of $H_2SO_4$ (as disclosed in U.S. Pat. No. 7,371,363). Preferably, the organic layer which contains minimal amount of HF is fed either directly to a dehydrochlorination reactor or further treated to remove the residual HF. Preferably, the crude HCFC-244bb stream is dehydrochlorinated using a vapor phase reactor containing dehydrochlorination catalyst. The catalyst is selected from $Cr_2O_3$, Sb/C, $FeCl_3$, $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$ and combinations thereof. Such a catalyst may also be a carbon- and/or metal-based catalyst, preferably activated carbon (in bulk or supported form), a nickel-based catalyst (such as Ni-mesh), metal halides, halogenated metal oxides, neutral (or zero oxidation state) metal or metal alloy and combinations of these. Other catalysts and catalyst supports may be used, including palladium on carbon, palladium-based catalyst (including palladium on aluminum oxides), and it is expected that many other catalysts may be used depending on the requirements of particular embodiments in view of the teachings contained herein. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$ $CaF_2$, LiCl, NaCl, KCl, CsCl and combinations thereof. Halogenation treatments can include any of those known in the prior art, particularly those that employ HF, $F_2$, HCl, $Cl_2$, HBr, $Br_2$, HI, and $I_2$ as the halogenation source. When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625. Optionally, the crude HCFC-244bb stream is dehydrochlorinated in a liquid phase reactor in the presence of an aqueous base solution. The aqueous base solution is preferably either NaOH or KOH, but other aqueous base solutions may likewise be used herein. See Scheme 2 in the FIGURE.

Preferably, the effluent containing HFO-1234yf, HCl and unreacted HCFC-244bb is deacidified in absorption equipment, dried, compressed and fed to a distillation train where HFO-1234yf is recovered and unreacted HCFC-244bb recycled to the dehydrochlorination reactor. Advantageously, a portion of any unreacted HCFC-244bb is recycled to the liquid phase reactor in order to purge HCFC-1233xf. Advantageously, the effluent containing HFO-1234yf, unreacted HCFC-244bb and water vapor is dried, compressed and fed to a distillation train where HFO-1234yf is recovered and unreacted HCFC-244bb recycled to dehydrochlorination reactor. Preferably, a portion of the unreacted HCFC-244bb is recycled to the liquid phase reactor in order to purge HCFC-1233xf.

BRIEF DESCRIPTION OF THE DRAWING

The FIGURE shows two block flow diagrams (Scheme 1 and Scheme 2) with processing steps used for the production of HFO-1234yf from TCP.

DETAILED DESCRIPTION OF THE INVENTION

The present invention can be generally described as an integrated process for the production of HFO-1234yf from TCP in three reaction steps wherein the first reaction is carried out at a higher pressure than the second reaction.

Key features of the integrated process of the present invention include operating the first step vapor phase fluorination reactor at a pressure sufficiently high such that no compression or isolation of intermediates is required for the subsequent liquid phase fluorination reactor. Also, the HCl gas generated in the first step is fed directly to the second step—both to promote mixing and to suppress over-fluorination in the second liquid phase fluorination reactor. The two fluorination reactors are operated with a large excess HF, typically on the order of 20 mol HF to 1 mol organic which, in the first step enhances the vaporization of TCP and minimizes byproduct formation and in the second step, minimizes byproduct formation. The terms "integrated process" describes how the process steps are coordinated such that no isolation of intermediate reactants is required. This provides a better yield than non-integrated processes, and reduces the operational costs of the process.

Scheme 1 in the FIGURE describes a process for the manufacture of HFO-1234yf from TCP in three integrated steps that include (R-1) hydrofluorination of TCP (tetrachloropropene) to HCFC-1233xf in the vapor phase at a higher pressure than the following step, followed by (R-2) hydrofluorination of HCFC-1233xf to HCFC-244bb in the liquid phase or liquid phase followed by vapor phase which is then followed by (R-3) dehydrochlorination in liquid or vapor phase to produce HFO-1234yf.

Preferably, in the Scheme 1 process, the vapor phase hydrofluorination is carried out at a higher pressure than the liquid phase hydrofluorination. Advantageously, in the Scheme 1 process, the TCP, HF and recycle is fed to a vapor phase reactor containing catalyst selected from the group consisting of $Cr_2O_3$, Sb/C, $FeCl_3$, $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$, or a mixture of such catalysts. As illustrated in Scheme 1, any HCl generated from the reaction is fed to the liquid phase hydrofluorination section. The reactor used for the hydrofluorination of TCP to HCFC-1233xf in the vapor phase is a reactor selected from the group consisting of; a single reactor, a multistage reactor, or a series of reactors; using a combination of recycle streams, fresh HF and fresh TCP.

As illustrated, the hydrofluorination of HCFC-1233xf to HCFC-244bb in the liquid phase further includes treatment of any reactor effluent containing HCFC-1233xf, HCl, excess HF and any unreacted TCP plus intermediates, by feeding this stream into a Quench/Recycle Column for separation of unreacted TCP and excess HF for recycle use in step (R-1) of the process. The HCFC-1233xf, HCl and HF is fed to a liquid phase reactor containing catalyst selected from $SbCl_3$, $SbCl_5$, $SbF_5$, $TiCl_4$, $SnCl_4$ for hydrofluorination of HCFC-1233xf to 1,1,1,2-tetrafluoro-2-chloropropane (HCFC-244bb). The hydrofluorination of HCFC-1233xf to HCFC-244bb in the liquid phase further includes treatment of any reactor effluent containing HCFC-1233xf and HCFC-244bb, by feeding this stream into a Quench/Recycle Column for separation of HCFC-1233xf for recycle use in step (R-2) of the process.

As illustrated, a mixture of HCFC-244bb, HCl, unreacted HCFC-1233xf and HF exit the liquid reactor system via a catalyst stripper which is used such that most of the unreacted HF and catalyst is refluxed back to the reactor. The effluent from the catalyst stripper may be passed through a bed containing catalyst for further conversion of HCFC-1233xf to HCFC-244bb. One preferred catalyst for this conversion is $SbCl_5$ supported on carbon. Preferably, the effluent from the catalyst stripper or the effluent from bed containing $SbCl_5$ supported on carbon is fed to an HCl column to separate essentially pure HCl in the overhead from the mixture of HCFC-244bb, HCFC-1233xf, HF and HCl. The essentially pure HCl product is either recovered as is or passed through silica gel for residual HF removal and absorbed into water. HF is recovered from a mixture of HCFC-244bb, HCFC-1233xf, and HF. One method for HF recovery is by cooling and phase separation to separate a layer rich in organics and a layer rich in HF. This method further includes HF recovery by phase separation and azeotropic distillation. Yet another method for the HF recovery is via absorption into sulfuric acid. Each of these options for HF recovery may be used, alone or in conjunction with the other.

In the process of the present invention, the organic layer which contains minimal amount of HF is fed either directly to a dehydrochlorination reactor or is deacidified. When the crude HCFC-244bb stream is dehydrochlorinated, a vapor phase reactor containing a dehydrochlorination catalyst selected from $Cr_2O_3$, Sb/C, $FeCl_3$, $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$ and combinations thereof is employed. Such a catalyst may also be a carbon- and/or metal-based catalyst, preferably activated carbon (in bulk or supported form), a nickel-based catalyst (such as Ni-mesh), metal halides, halogenated metal oxides, neutral (or zero oxidation state) metal or metal alloy and combinations of these. Other catalysts and catalyst supports may be used, including palladium on carbon, palladium-based catalyst (including palladium on aluminum oxides), and it is expected that many other catalysts may be used depending on the requirements of particular embodiments in view of the teachings contained herein. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, CsCl and combinations thereof. Halogenation treatments can include any of those known in the prior art, particularly those that employ HF, $F_2$, HCl, $Cl_2$, HBr, $Br_2$, HI, and $I_2$ as the halogenation source. When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

As illustrated in Scheme 2 of the FIGURE, when the crude HCFC-244bb stream is dehydrochlorinated in a liquid phase reactor, an aqueous base solution is employed. The aqueous base solution is preferably either NaOH or KOH. When the effluent containing HFO-1234yf, HCl and unreacted HCFC-244bb is deacidified in absorption equipment, dried, compressed and fed to a distillation train, HFO-1234yf is recovered and unreacted HCFC-244bb is recycled to the dehydrochlorination reactor. Preferably, a portion of any unreacted HCFC-244bb is recycled to the liquid phase reactor in order to purge HCFC-1233xf. When the effluent containing HFO-1234yf, unreacted HCFC-244bb and water vapor is dried, compressed and fed to a distillation train, HFO-1234yf is recovered and unreacted HCFC-244bb is recycled to dehydrochlorination reactor. Preferably, a portion of the unreacted HCFC-244bb is recycled to the liquid phase reactor in order to purge HCFC-1233xf.

A detailed description of one preferred embodiment of the integrated process of the present invention is as follows:

(1) Hydrofluorination of TCP to 2-chloro-3,3,3,-trifluoropropene (HCFC-1233xf) using a single reactor or a multistage reactor or a series of reactors in the vapor phase containing catalyst using a combination of recycle stream(s), fresh HF and fresh TCP as illustrated in the FIGURE (at Scheme 1) as "R-1, Step 1 Reactor". In the preferred embodiment, the reaction is carried out under conditions effective to provide at least 50% conversion, preferably 80-85% conversion of TCP to HCFC-1233xf where the mole ratio of HF to TCP is about 20:1, reaction temperature is about 300° C. and pressure is about 120 psig.

(2) Cool the above (1) reactor effluent containing HCFC-1233xf, HCl, excess HF and any unreacted TCP plus intermediates and feed this stream into a Quench/Recycle Column for separation of unreacted TCP plus intermediates and excess HF for recycle to (1) and; HCFC-1233xf, HCl and HF to liquid phase reactor (3), as illustrated in the FIGURE (at Scheme 1) as "R-2 Step 2 Reactor".

(3) Feed the HCFC-1233xf, HCl and HF to a liquid phase reactor containing catalyst (see the catalyst choices listed above) for hydrofluorination of HCFC-1233xf to 1,1,1,2-tetrafluoro-2-chloropropane (HCFC-244bb). In the preferred embodiment, the reaction is carried out under conditions effective to provide at least 96% conversion, preferably 98% conversion of HCFC-1233xf to HCFC-244bb where the mole ratio of HF to TCP is about 20:1, reaction temperature is about 85° C. and pressure is about 100 psig.

(4) A mixture of HCFC-244bb, HCl, unreacted HCFC-1233xf and HF exit the liquid reactor system via a catalyst stripper which is used such that most of the unreacted HF and catalyst is refluxed back to the reactor.

(5) The effluent from the catalyst stripper may be passed through a bed containing $SbCl_5$/Carbon catalyst for further conversion of HCFC-1233xf to HCFC-244bb in order to achieve a total of 98% conversion as stated in (3) above.

(6) The effluent from the catalyst stripper (4) or the effluent from SbCl5/C bed (5) is fed to an HCl column to separate essentially pure HCl in the overhead from the mixture of HCFC-244bb, HCFC-1233xf, HF and HCl.

(7) The essentially pure HCl product from (6) above may be recovered as is or passed through silica gel for residual HF removal and absorbed into water.

(8) The mixture of HCFC-244bb, HCFC-1233xf, HF from (6) above is fed to an HF recovery system to separate a stream rich in organic and a stream rich in HF. Such methods include phase separation and preferential absorption of HF into sulfuric acid.

(9) The organic stream which contains minimal amount of HF is fed either directly to a dehydrochlorination reactor or further deacidified before being fed to the dehydrochlorination reactor (10) below.

(10) The HCFC-244bb stream is dehydrochlorinated using a vapor phase reactor containing dehydrochlorination catalyst. In the preferred embodiment, the reaction is carried out under conditions effective to provide at least 20% conversion, preferably at least 50% conversion of HCFC-244bb to HFO-1234yf where the reaction temperature is about 400° C. and pressure is about 15 psig. Optionally, this stream may be dehydrochlorinated in a liquid phase reactor in the presence of an aqueous base solution such as NaOH or KOH at temperatures of about 50° C. See Scheme 2 in the FIGURE.

(11) If a vapor phase dehydrochlorination reactor is used, the effluent from (10) above containing HFO-1234yf, HCl and unreacted HCFC-244bb is deacidified in absorption equipment (KOH or NaOH scrubbing), dried with 3A mole sieves or another suitable drying agent, compressed and fed to a distillation train where HFO-1234yf is recovered and unreacted HCFC-244bb recycled to dehydrochlorination reactor (10) above. A portion of the unreacted HCFC-244bb may be recycled to the liquid phase reactor (3) in order to purge this section of HCFC-1233xf.

(12) If a liquid phase dehydrochlorination reactor is used, the effluent from (10) above containing HFO-1234yf, unreacted HCFC-244bb and water vapor is dried with a suitable drying agent, compressed and fed to a distillation train where HFO-1234yf is recovered and unreacted HCFC-244bb recycled to dehydrochlorination reactor (10) above. A portion of the unreacted HCFC-244bb may be recycled to the liquid phase reactor (3) in order to purge this section of HCFC-1233xf.

EXAMPLE

The following non-limiting example is prospective and represents results obtained from standard process simulation and physical property prediction procedures in order to illustrate the invention. In the table below:
"R-1 Inlet" is the stream fed to the first hydrofluorination reactor.
"R-1 Exit" is the resulting effluent with reactor operating under preferred conditions.
"Quench Overhead" and "R-1 Recycle" respectively are the overhead and bottoms streams exiting a distillation tower whose primary purpose is to separate TCP and HF from the reaction products for recycle back to the first hydrofluorination reactor.

TABLE 1

R-1
Composition percentages, wt % for various streams

|  | R-1 Inlet | R-1 Exit | Quench Overhead | R-1 Recycle |
|---|---|---|---|---|
| Temperature ° C. | 300 | 300 | 48.8 | 93.9 |
| Pressure psig | 119.73 | 119.5 | 110 | 110 |
| TCP + 1231 + 1232 | 33.9% | 5.7% | 0.0% | 10.1% |
| HF | 65.8% | 56.2% | 14.2% | 89.3% |
| HCl | 0.0% | 17.3% | 39.3% | 0.0% |
| 245cb | 0.3% | 0.8% | 1.1% | 0.6% |
| 244bb | 0.0% | 0.0% | 0.0% | 0.0% |
| 1234yf | 0.0% | 0.1% | 0.2% | 0.0% |
| 1233xf | 0.0% | 19.8% | 45.1% | 0.0% |

In the table below:
"R-2 Inlet" is the stream fed to the second hydrofluorination reactor.
"R-2 Exit" is the resulting effluent with reactor operating under preferred conditions.
"Recovered HCl" is the overhead stream from a distillation tower whose primary purpose is to separate HCl from a mixture of reactants and reaction products.
"R-2 Recycle" is the stream resulting from the HF Recovery section of the process. It is the resulting stream from subjecting the bottoms of the above distillation tower to HF recovery.

TABLE 2

R-2
Composition percentages, wt % for various streams

|  | R-2 Inlet | R-2 Exit | Recovered HCl | R-2 Recycle |
|---|---|---|---|---|
| Temperature ° C. | 85 | 61.9 | −42.8 | 85 |
| Pressure psig | 100 | 100 | 80 | |
| TCP + 1231 + 1232 | 0.0% | 0.0% | 0.0% | 0.0% |
| HF | 49.8% | 46.0% | 21 ppm | 93.8% |
| HCl | 21.6% | 21.7% | 99.80% | 0.0% |
| 245cb | 0.6% | 1.2% | 0.0% | 0.0% |
| 244bb | 3.0% | 30.4% | 0.19% | 6.1% |
| 1234yf | 0.1% | 0.1% | nil | 0.0% |
| 1233xf | 24.8% | 0.5% | 0.0% | 0.1% |

In the table below:
"R-3 Inlet" is the stream fed to the dehydrochlorination reactor.
"R-3 Exit" is the resulting effluent with reactor operating under preferred conditions.
"1234yf Product" is the recovered product from a purification train.
"R-3 Recycle" is a stream resulting from the purification train. In this example, this stream is recycled to the dehydrochlorination reaction. Optionally, a portion of it (or all of it) may be recycled to the second hydrofluorination reactor to reduce the HCFC-1233xf content.

TABLE 3

R-3
Composition percentages, wt % for various streams

|  | R-3 Inlet | R-3 Exit | 1234yf Product | R-3 Recycle |
|---|---|---|---|---|
| Temperature ° C. | 400 | 400 | 27.1 | 86.9 |
| Pressure psig | 15 | 15 | 90 | |
| TCP + 1231 + 1232 | 0.0% | 0.0% | 0.0% | 0.0% |
| HF | 0.0% | 0.1% | 0.0% | 0.0% |
| HCl | 0.0% | 3.6% | 0.0% | 0.0% |
| 245cb | 0.7% | 0.4% | 0.5% | 0.0% |
| 244bb | 73.3% | 58.2% | 0.0% | 68.9% |
| 1234yf | 0.1% | 11.5% | 99.5% | 0.0% |
| 1233xf | 25.9% | 26.3% | 0.0% | 31.1% |

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:
1. A process for the manufacture of HFO-1234yf from 1,1,2,3-tetrachloropropene (TCP) in three integrated steps comprising;
hydrofluorinating TCP in a vapor phase at a first pressure to form an HCFC-1233xf containing effluent comprising HCFC-1233xf and HCl;
hydrofluorinating HCFC-1233xf in a liquid phase or a liquid phase followed by vapor phase at a second pressure that is lower than the first pressure to form an HCFC-244bb containing effluent, wherein HCl from the HCFC-1233xf containing effluent is also provided to the hydrofluorination of HCFC-1233xf; and
dehydrochlorinating HCFC-244bb in a liquid or vapor phase to produce a HFO-1234yf containing effluent.

2. The process of claim 1, wherein the TCP is hydrofluorinated in the presence of a catalyst selected from the group consisting of $Cr_2O_3$, Sb/C, $FeCl_3$, $Cr_2O_3/Al_2O_3$, $Cr_2O_3/AlF_3$, $Cr_2O_3/C$, $CoC_2/Cr_2O/Al_2O_3$, $NiCl_2/Cr_2O_3/Al_2O_3$, $CoCl_2/AlF_3$ and combinations thereof.

3. The process of claim 1, wherein the hydrofluorination of TCP occurs in a reactor selected from the group consisting of a single reactor, a multistage reactor, or a series of reactors, using a combination of one or more recycle streams, HF and TCP.

4. The process of claim 1, wherein the HCFC-1233xf containing effluent further comprises HCl, excess HF and unreacted TCP.

5. The process of claim 4, wherein unreacted TCP is separated from the HCFC-1233xf effluent and recycled.

6. The process of claim 1, wherein HCFC-1233xf is hydrofluorinated in the presence of a catalyst selected from the group consisting of $SbCl_3$, $SbCl_5$, $SbF_5$, $TiCl_4$, $SnCl_4$ and combinations thereof.

7. The process of claim 1, wherein the HCFC-244bb containing effluent further comprises HCl, excess HF, and unreacted HCFC-1233xf.

8. The process of claim 7, wherein unreacted HCFC-1233xf is separated from the HCFC-244bb effluent and recycled.

9. The process of claim 7, wherein the HCFC-244bb effluent is treated with a catalyst stripper to remove unreacted HF and any catalyst that is present.

10. The process of claim 9, wherein the unreacted HF and catalyst are recycled.

11. The process of claim 9, wherein, after treatment with the catalyst stripper, HCl is removed from the HCFC-244bb effluent.

12. The process of claim 7, wherein, after treatment with the catalyst stripper, the unreacted HCFC-1233xf in the HCFC-244bb effluent is hydrofluorinated in the presence of a catalyst to form a second HCFC-244bb effluent.

13. The process of claim 12, wherein the catalyst is $SbCl_5$ supported on carbon.

14. The process of claim 12, wherein, after the unreacted HCFC-1233xf is hydrofluorinated, HCl is removed from the second HCFC-244bb effluent.

15. The process of claim 7, wherein excess HF is recovered from the HCFC-244bb effluent.

16. The process of claim 15, wherein HF is recovered by cooling and phase separation of the HCFC-244bb effluent to provide a first layer rich in organics and a second layer rich in HF.

17. The process of claim 15, wherein the HF is recovered by phase separation and azeotropic distillation.

18. The process of claim 15, wherein the HF is recovered by absorption into sulfuric acid.

19. The process of claim 1, wherein HCFC-244bb is dehydrochlorinated in the vapor phase in the presence of a catalyst comprising $Cr_2O_3$.

20. The process of claim 1, wherein HCFC-244bb is dehydrochlorinated in the vapor phase in the presence of at least one metal halide catalyst.

21. The process of claim 20, wherein the metal halide catalyst is a mono-, bi-, or tri-valent metal halide.

22. The process of claim 20, wherein a component metal of the metal halide catalyst is selected from the group consisting of $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$ and a component halogen of the metal halide catalyst is selected from the group consisting of $F^-$, $Cl^-$, $Br^-$, and $I^-$.

23. The process of claim 20, wherein the metal halide catalyst is selected from the group consisting of LiF, NaF, KF, CsF, $MgF_2$, $CaF_2$, LiCl, NaCl, KCl, CsCl and combinations thereof.

24. The process of claim 1, wherein HCFC-244bb is dehydrochlorinated in the liquid phase in the presence of an aqueous base solution.

25. The process of claim 24, wherein the aqueous base solution is either NaOH or KOH.

26. The process of claim 1, wherein the HFO-1234yf effluent further comprises HCl and unreacted HCFC-244bb.

27. The process of claim 26, wherein the HFO-1234yf effluent is deacidified in absorption equipment, then dried and compressed.

28. The process of claim 27 wherein HFO-1234yf is recovered and unreacted HCFC-244bb is recycled.

* * * * *